United States Patent [19]

Hall

[11] 4,302,185
[45] Nov. 24, 1981

[54] LIQUID CONTROL SYSTEM

[76] Inventor: Arthur L. Hall, 520 Bardon Rd., Knoxville, Tenn. 37919

[21] Appl. No.: 58,844

[22] Filed: Jul. 19, 1979

[51] Int. Cl.³ .............................................. A61C 1/00
[52] U.S. Cl. ...................................... 433/27; 433/84; 433/98; 222/95; 173/60; 417/403
[58] Field of Search ................. 433/27, 82, 84, 85, 433/87, 98, 99, 100; 222/95; 173/60; 417/479, 403, 404

[56] References Cited

U.S. PATENT DOCUMENTS

| 285,477 | 9/1883 | Garsed | 417/479 |
|---|---|---|---|
| 2,772,817 | 12/1956 | Jauch | 417/479 |
| 2,986,898 | 6/1961 | Wood, Jr. | 417/404 |
| 3,093,082 | 6/1963 | Ziegler | 417/479 |
| 3,129,511 | 4/1964 | Williams | 433/87 |
| 3,237,306 | 3/1966 | Staunt | 433/84 |
| 3,413,875 | 12/1968 | Larson | 173/60 |
| 3,431,081 | 3/1969 | Edwards et al. | 417/403 |
| 3,505,737 | 4/1970 | Merolla | 433/27 |
| 3,949,753 | 4/1976 | Dockhorn | 222/95 |
| 4,033,479 | 7/1977 | Fletcher et al. | 222/95 |

*Primary Examiner*—Gene Mancene
*Assistant Examiner*—John J. Wilson
*Attorney, Agent, or Firm*—Luedeka & Fitch

[57] ABSTRACT

A system for concurrently supplying a liquid and drive gas to a gas-driven tool includes a drive gas source and conduit means connecting the drive gas source to the tool. Exhaust conduit means connect the tool to exhaust sensor means. A liquid source is connected to the tool by liquid conduit means. Means for causing liquid to flow from the liquid source to the tool is activated by means responsive to pressure of over a predetermined value at the exahust gas sensor.

3 Claims, 4 Drawing Figures

LIQUID CONTROL SYSTEM

The present invention relates generally to improvements in the field of dental and surgical equipment and more particularly to apparatus for concurrent provision of pressurized liquid and gas to dental and surgical tools. The present invention has particular application to systems requiring sterile liquids.

In the fields of dentistry and surgery, a variety of hand tools are used, many of which are driven by pressurized gas. Various control systems have been developed for selectively supplying several fluids, in addition to drive gas, to one or more tools. Such additional fluids include chip air (low pressure air for clearing a work site) and liquids.

In the course of using dental and surgical tools, it is frequently desirable to apply a liquid, usually water, to the work site either as a coolant or a wetting agent for surrounding tissue. In many applications distilled water, or even tap water, is an acceptable liquid. Accordingly, many systems includes means for supplying such liquids from a source such as a rigid bottle into which pressurized gas is introduced to provide a pressurized liquid source. In addition, means are included in such control systems for controlling the flow of such pressurized liquids. Such flow control means may comprise, for example, a manually operable valve disposed in the conduit connecting the pressurized liquid source to the tool. However, most operators desire automatic control of fluid flow so that the fluid flows whenever the tool is operated, without the necessity for separate steps to initiate and stop liquid flow. For those tools for which the drive air flow to the tool is controlled by a foot pedal, liquid flow can be simultaneously controlled by a gas-controlled liquid valve in the constantly pressurized liquid line. Downstream of the foot pedal, a branch of the conduit means supplying drive gas to the tool is connected to the gas-controlled liquid valve so that the flow of pressurized liquid to the tool is controlled concurrently with the flow of drive gas to the tool.

For those tools which are controlled by hand at the tool, rather than by a foot pedal, such prior liquid control systems are not suitable. The pressure in the drive gas conduit is essentially constant, all the way to the tool so that there is no pressure change to open and close a liquid valve. Thus, concurrent drive gas and liquid flow have not been available for hand-controlled tools.

Furthermore, in some dental operations and essentially all surgical operations even distilled water is unacceptable. Only sterile liquids may be used at the work site. However, inasmuch as the entire control systems cannot reasonably be maintained in sterile condition, sterile liquids cannot be supplied through, and be directly controlled by, the prior control systems. Instead, sterile liquid supplies have been pressurized and controlled manually. Sterile solutions are supplied for surgical use in flexible, stabilized plastic bags to which flexible tubing is connected at one end. The entire unit is sterile and the distal end of the tubing is directly attached to the sterile dental or surgical tool in use. Heretofore, the general practice has been for a nurse or technician to manually squeeze the resilient bag whenever the tool is operated, thus forcing the sterile solution from the bag, through its individual tubing, and to the tool. Then when the sterile solution is no longer required, the nurse or technician releases the pressure on the bag and the flow subsides.

Obviously, such manual operation is not desirable primarily because it requires the presence of an extra person in the surgical area. The person responsible for applying the pressure to the bag cannot have any other duties which may conflict with this duty. Furthermore, it is particularly desirable that the liquid be applied simultaneously with the action of the tool, i.e. whenever drive gas is supplied to the tool. The communication with the nurse or technician to control the sterile liquid flow inherently involves a time lag and also the nurse or technician may be distracted at one time or another and thus fail to provide the sterile solution as required.

It is therefore an object of the present invention to provide apparatus for supplying a sterile solution to a dental or surgical tool. It is also an object to provide apparatus for concurrently supplying drive gas and sterile liquid to dental and surgical tools. It is a further object to provide apparatus for concurrently controlling the supplies of a liquid and drive gas to a hand-controlled tool. Further objects and advantages will become apparent by reference to the following description and accompanying drawings.

Figure 1:
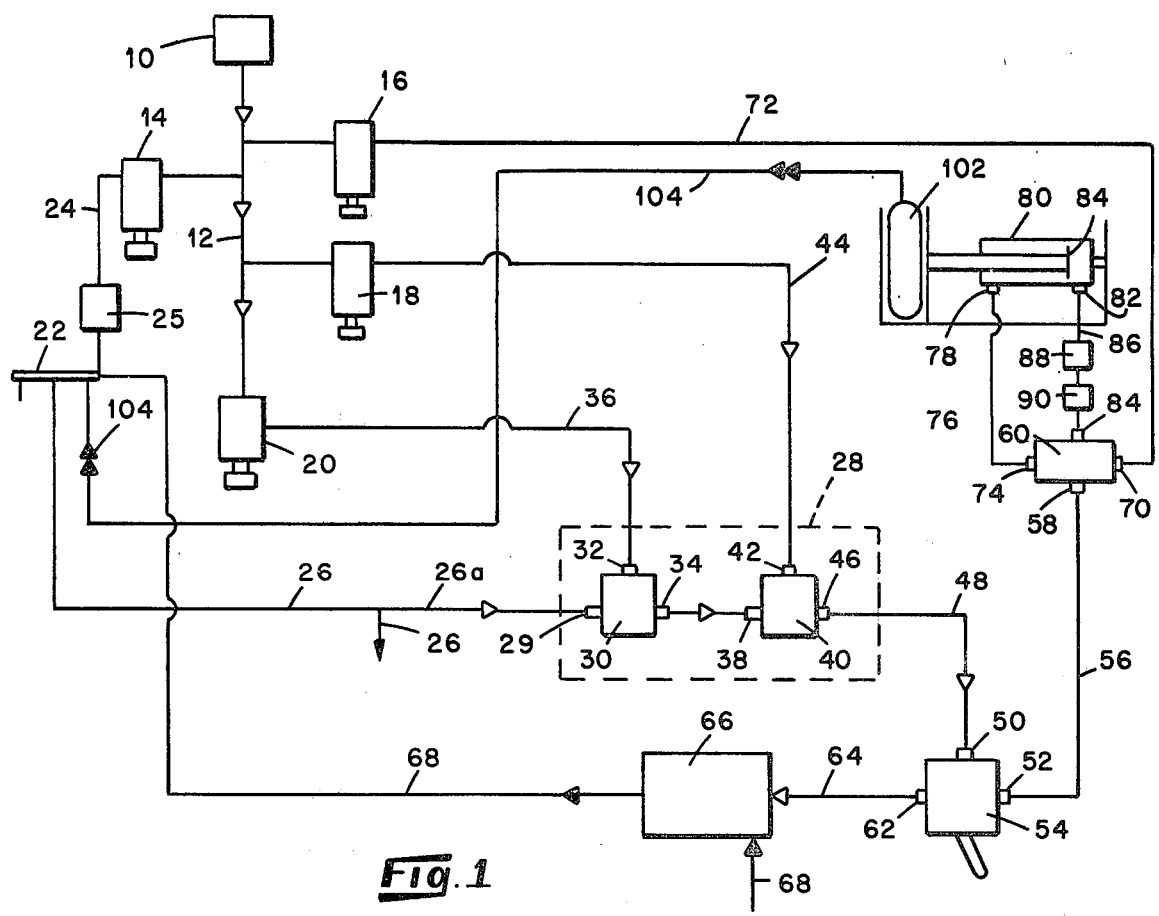
FIG. 1 is a schematic diagram of a sterile liquid supply system embodying various of the features of the present invention.
Figure 2:
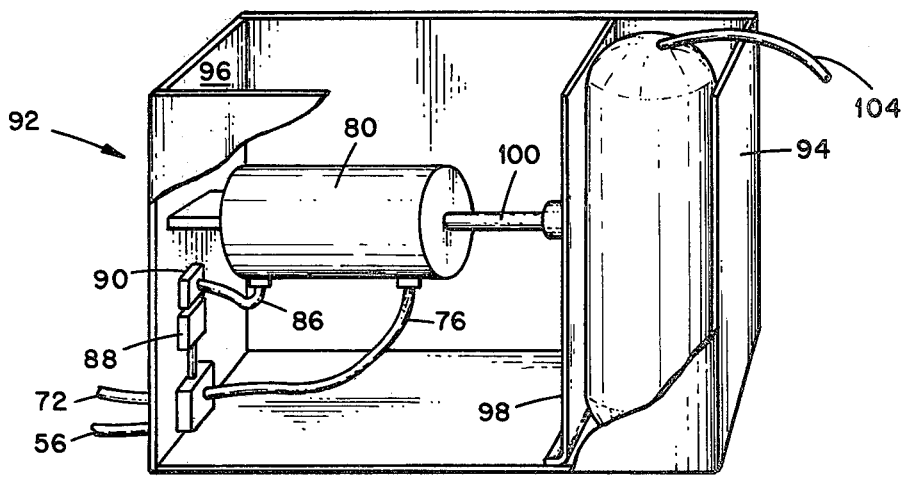
FIG. 2 is a perspective view, partially broken away, of a gas activatable liquid source embodying various of the features of the present invention.

Generally, in accordance with the present invention the operation of the tool is detected from the extremely low pressure exhaust gas, i.e. the spent drive gas, which exits from the tool. In response to this detection, a liquid source, which, for example, may be a gas-operable liquid switch in a pressurized liquid conduit or means including a gas-activatable cylinder adapted to pressurize a flexible liquid-containing vessel, is activated to supply liquid to the tool. Then, when the operation of the tool ceases and the exhaust gas flow ceases, the liquid source is deactivated and liquid flow ceases.

Referring to the drawings, a main gas source 10, which may comprise a cylinder of compressed nitrogen or a source of compressed air, for example, is connected directly through the main gas conduit 12 to a drive gas regulator 14, a pressurizing gas regulator 16, an activating gas regulator 18 and an amplifying gas regulator 20.

The drive gas regulator 14 is connected to a gas powered tool 22, e.g. a surgical drill, which is either hand-controlled or foot-controlled, through drive gas conduit means 24, which may include suitable control means 25, such as those disclosed in U.S. Pat. No. 4,145,813, and my copending application Ser. No. 965,787, filed Dec. 4, 1978. The exhaust outlet of the tool 22 is vented to the atmosphere through exhaust conduit means 26. The conduit 26 also includes a branch conduit 26a which provides communication between the conduit 26 and sensor means 28. The sensor means 28 are adapted to provide activating air, at a pressure of about 30–35 psig to a liquid source in response to the flow of exhaust gas from the tool at pressures as low as about 0.04 psig.

In a preferred embodiment, the exhaust conduit branch 26a is connected to the low pressure inlet 29 of a low pressure gas amplifier 30 having an amplifying gas inlet 32, a relief outlet 31, and an amplified gas outlet 34.

Figure 3:
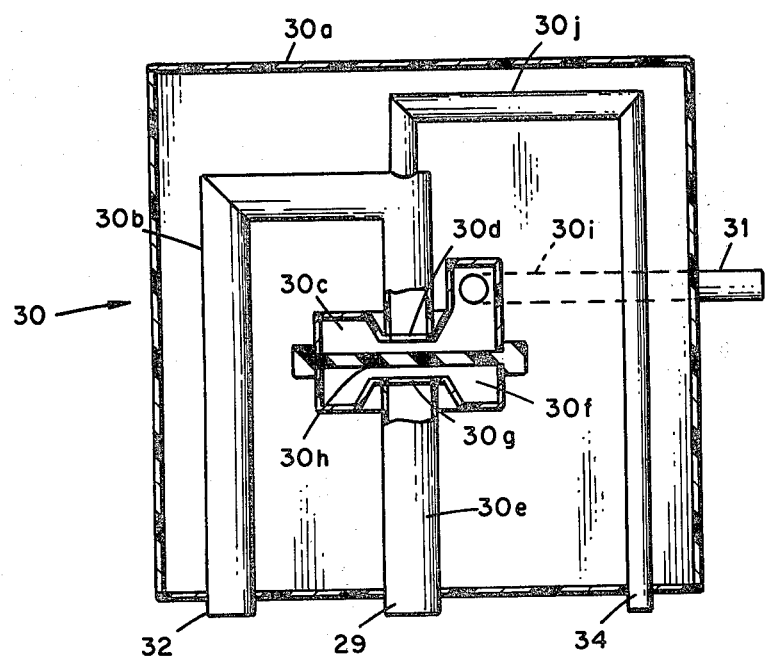
FIG. 3 is a vertical cross-sectional view through the center of a low pressure gas amplifier for use in accordance with the present invention.

As shown particularly in FIG. 3, a suitable low pressure amplifier includes a housing 30a having defined therein a plurality of passageways connecting the inlets 29 and 32 and the outlets 31 and 34. The amplifying gas inlet 32 is connected by a passageway 30b to a chamber 30c at an opening 30d. The low pressure inlet 29 is connected by a passageway 30e to a chamber 30f at an opening 30g. A diaphragm 30h is secured within the housing 30a to provide a common wall between the chambers 30c and 30f. The diaphragm 30h, in its normally relaxed position, is parallel to and slightly spaced from the opening 30d. The relief outlet 31 is connected by a passageway 30i to the chamber 30c. The amplified gas outlet 34 is connected to the amplifying gas inlet 32 by the passageway 30b and a passageway 30j.

In its inactivated condition, when exhaust gas is not flowing to the low pressure gas inlet 29, amplifying gas received from the regulator 20 through conduit means 36 flows from the inlet 32 through the passageway 30b and opening 30d into the chamber 30c. From the chamber 30c, the amplifying gas enters the passageway 30i and exits to the atmosphere through the outlet 31, rather than exit through the passageway 30j and the outlet 34, which is connected to high pressure amplifier 40 through conduit 37.

When exhaust gas enters the passageway 30e, from the inlet 29, it is directed into the chamber 30f, where the gas displaces the diaphragm 30h. The area and flexibility of the diaphragm 30h are such that the low pressure of the exhaust gas is sufficient to overcome the amplifying gas pressure within the chamber 30c because the amplifying gas is vented to the atmosphere through the outlet 31. Displacement of the diaphragm covers the opening 30d to require the amplifying gas to flow through passageway 30j to the outlet 34.

The amplified gas outlet 34 of the low pressure amplifier is connected through conduit means 37 to the amplified gas inlet 38 of a high pressure gas amplifier 40 having an activating gas inlet 42. The inlet 42 is connected by conduit means 44 to the activating gas regulator 18. An activating gas outlet 46 of the amplifier 40 is connected by conduit means 48 to the inlet 50 of a disable switch 52. The amplifier 40 also includes first and second relief outlets 41 and 43.

Figure 4:
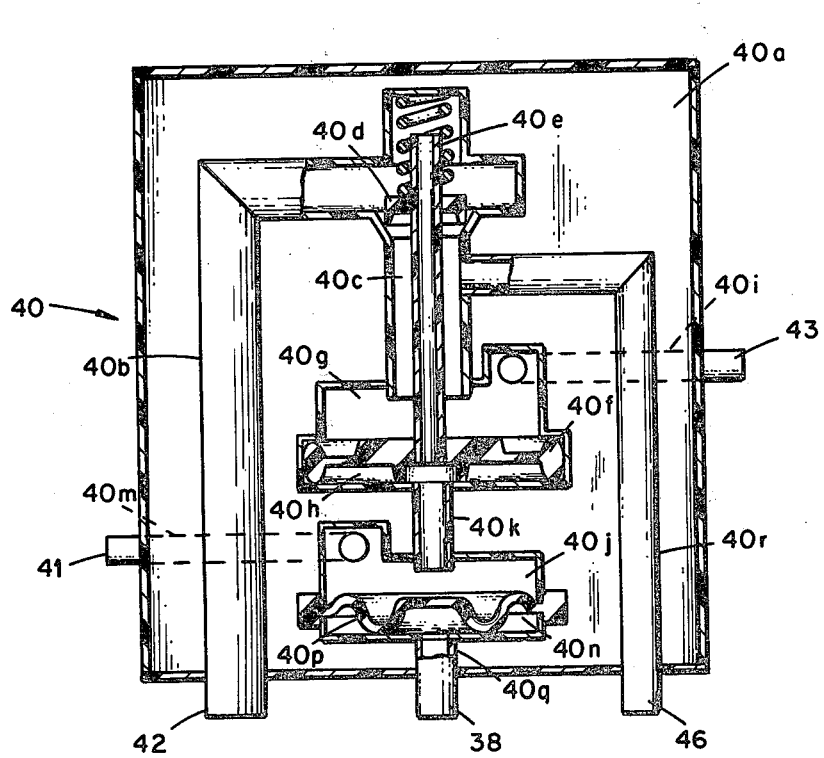
FIG. 4 is a vertical cross-sectional view through the center of a high pressure gas amplifier for use in accordance with the present invention.

As shown particularly in FIG. 4, a suitable high pressure amplifier includes a housing 40a having defined therein a plurality of passageways connecting the inlets 38 and 42 and the outlets 41, 43 and 46. The activating gas inlet 42 is connected by a passageway 40b to a central passageway 40c. Direct communication between the passageway 40b and passageway 40c is initially blocked by a spring-loaded plunger 40d including a hollow elongated shaft 40e longitudinally disposed within the passageway 40c. A first diaphragm 40f is radially secured to the hollow shaft 40e. The diaphragm 40f is peripherally secured to the housing 40a to define a first chamber 40g and a second chamber 40h on either side thereof. The chamber 40h is in communication with the passageway 40b only through the hollow shaft 40e. The chamber 40g is in communication with the outlet 43 through the passageway 40i.

The chamber 40h is also in communication, through passageway 40k, with a third chamber 40j which is in turn connected to relief outlet 41 through a passageway 40m.

The third chamber 40j is separated from a fourth chamber 40n by a second diaphragm 40p which provides a flexible common wall therebetween. The diaphragm 40p is peripherally secured to the housing 40a. The fourth chamber 40n is connected to the inlet 38 by a passageway 40q.

The activating gas outlet 46 is connected to the passageway 40c by a passageway 40r which joins the passageway 40c at a point between the junction of the passageways 40b and 40c and the junction of the passageway 40c and the chamber 40g.

In its activated condition, when amplifying gas does not flow to the inlet 38 from the low pressure amplifier 30, activating gas received from the regulator 18 through the conduit 44 flows from the inlet 42, through the passageway 40b, through the hollow shaft 40e to the second chamber 40h. From the chamber 40h, the amplifying gas flows through the passageway 40k to the third chamber 40j and vents outwardly to the atmosphere through the passageway 40m and the outlet 41. The size of the passageway 40m is restricted such that a back pressure is developed within the chamber 40h, thus displacing the diaphragm 40f. Displacement of the diaphragm 40f simultaneously moves the plunger 40d longitudinally a sufficient distance to permit direct air flow from the passageway 40b to the outlet 43 through the passageway 40c and the chamber 40g. At this point the plunger 40d does not move a distance sufficient to cause the diaphragm 40f to prevent air flow from the passageway 40c to the chamber 40g. Thus, in the inactivated condition, the amplifier 40 freely vents activating gas from the outlets 41 and 43.

When the amplifier 40 is in the activated condition, i.e. when amplifying gas is received from the low pressure amplifier at the inlet 38, the amplifying gas flows through the passageway 40q to the chamber 40n. The pressure of the amplifying gas in the chamber 40n displaces the diaphragm 40p and prevents activating gas flow from the passageway 40k to the chamber 40j. The extended area of the diaphragm 40p, as compared to the crosssectional area of the passageway 40k, permits the amplifying gas to overcome the higher pressure activating gas.

Simultaneously, however, the prevention of the escape of activating gas through the outlet 41 causes the gas pressure within the chamber 40h to increase, further displacing the diaphragm 40f beyond its inactivated position. The diaphragm 40f is displaced a distance sufficient to prevent activating gas flow from the passageway 40c to the chamber 40g. Instead, the activating gas flows from the passageway 40c, through the passageway 40r to the outlet 46. A suitable high pressure amplifier is available from the Festo Corporation of Port Washington, N.Y., under the designation No. 007098.

The disable switch 52 may comprise an on-off gas valve having only a first outlet 54 connected by conduit means 56 to an activating gas inlet 58 of an activating switch 60 of a gas-activatable liquid source. In this event in one position the disable switch 52 permits gas to flow from the inlet 50 to the outlet 54. In the other position such flow is prevented.

In a system providing greater flexibility, as shown in FIG. 1, the disable switch 52 is a three position valve and includes a second outlet 62, mutually exclusive from the first outlet 54, which is connected by conduit means 64 to a gas-activated liquid control valve 66 in a pressurized liquid line 68 carrying distilled water, for example. In this system activating gas from switch inlet 50 can be isolated from the system or caused to pass through either outlet 54 or 62, as desired. Unlike the prior systems for concurrently supplying drive gas and liquid to a tool, the drive gas conduit to the tool is not interrupted or branched downstream of the drive gas regulator to provide gas to the liquid control valve.

The activating switch 60 for a gas-activatable liquid source includes an activating gas inlet 58, a pressurizing gas inlet 70, a first pressurizing gas outlet 74, and a quick exhaust outlet 90. The gas inlet 58 comprises a poppet valve. The pressurizing gas inlet 70 is connected to the pressurizing gas regulator 16 by conduit means 72. The outlet 74 is connected by conduit means 76 to a retraction inlet 78 of a two-way gas cylinder 80 having an extension inlet 82. The outlet 87 is connected by conduit means 86 to the extension inlet 82. A piston 84 is disposed within the cylinder 80, between the extension inlet 82 and the retraction inlet 78 so that the piston 84 and its attached piston rod 85 are movable between an extended position and a retracted position by means of gas pressure applied through the respective extension inlet 82 and retraction inlet 78. Preferably, an extension pressure regulator 88 is included in the conduit means 86 to prevent an excessive extension pressure within the cylinder 80. The quick exhaust outlet 90 exhausts gas contained in the cylinder to permit rapid extension and retraction of the piston 84.

The gas cylinder 80 is securely mounted within a rigid box 92, preferably made from stainless steel, rigid plastic, or the like, and including a first end wall 94, a second end wall 96 which is parallel to the first wall 94, and said walls 97a and 97b connecting the end walls. A plate 98 is slidably received within the box 92 in a position between and parallel to the first end wall 94 and second end wall 96, defining a vessel receiving zone 99 between the plate 98 and the first end wall 94. The gas cylinder 80 is fixedly attached at one end 100 to the second end wall 96 and the piston rod 85, extending axially from the piston 84, is fixedly attached to the plate 98. Thus, the relative spacing between the plate 98 and first end wall 94 are variable in accordance with the degree of extension of the piston rod 85 from the gas cylinder 80.

The vessel receiving zone 99 between the plate 98 and the first wall 94 is adapted to slidingly receive and substantially surround a one-liter elongated vessel 102 of sterile solution when the piston is in the retracted position. The vessel 102 preferably comprises a flexible, yet inelastic, plastic material such as polyvinyl chloride and is connected at one end, by a liquid supply conduit 104, to the tool 22. Such vessels are standard commercially available items in the medical field. When the vessel is inserted into the vessel receiving zone, the conduit 104 preferably extends from the uppermost portion of the vessel 102.

In operation, drive gas is supplied to the tool 22 through conduit means 24 at a pressure of 30–150 psig, depending upon the tool and type of operation. Suitable control means 25, such as a manifold and valves for supplying a plurality of tools and fluids, are included in the conduit means 24 as known to the art. After driving the tool, the spent gas is exhausted through the conduit 26 to the atmosphere. The position of the connection between the exhaust conduit 26 and the branch conduit 26a is such that a relatively small pressure, e.g. 0.5 psig, is supplied to the inlet 29 of the low pressure amplifier 30.

Amplifying gas, at a preferred pressure of about 1.5 psig, is received by the low pressure amplifier 30 from the amplifying gas regulator 20 through the conduit 36. When exhaust gas from the conduit 26a is received at the low pressure amplifier, i.e. when the tool is being driven, the amplifying gas under pressure is applied to the inlet 38 of the high pressure amplifier 40. However, until the tool 22 reaches a predetermined speed, so that the exhaust gas pressure in the branch 26a reaches about 0.5 psig, the low pressure amplifier 30 does not direct amplifying gas to the amplifier 40.

Activating gas, at a pressure of about 30–35 psig, is received by the high pressure amplifier 40 from the activating gas regulator through the conduit 44. When amplifying gas from the low pressure amplifier 30 is received at the inlet 38 of the high pressure amplifier 40, activating gas is caused to flow from conduit 44 through conduit 48 to the switch 52.

If a non-sterile liquid is desired for the tool 22, the switch 52 is set to direct the activating gas from conduit 48 through conduit 64 to the liquid control valve 66, which is opened to permit non-sterile liquid to flow to the tool concurrently with the sensing of exhaust gas from the tool 22. When the pressure in the exhaust conduit 26 drops as the tool is deactuated, the low pressure amplifier 30 cuts off the supply of the activating gas which in turn closes the valve 66 shutting off the liquid supply. This occurs regardless of whether the tool is hand-controlled or foot-controlled.

If sterile liquid is required at the tool, the switch 52 is set to direct the activating gas from the conduit 48 through the conduit 56 to the activating switch 60 of the sterile liquid pressurizing means. Pressurizing gas, at a pressure of about 80 psig, is received by the activating switch 60 from the pressurizing gas regulator 16 through the conduit 72. When activating gas is received by the activating switch 60, i.e. when the pressure in exhaust conduit 26 is over a predetermined level, pressurizing gas is directed by the activating switch 60 to the extension inlet 82 of the cylinder 80, effecting extension of the piston rod 85. Simultaneously, gas contained within the cylinder 80, between the piston 84 and the retraction inlet 78, are expelled through the exhaust outlet 90. As the piston rod 85 extends, the flexible vessel 102 is squeezed between the plate 98 and the first wall 94, pressurizing the vessel 102 and causing the sterile liquid contained in the vessel to flow through the sterile conduit 104 to the tool 22–without ever contacting a non-sterile or non-disposable surface. The squeezing force applied to the vessel is controlled by the extension pressure regulator 88 located in the conduit 86 to prevent excess pressure from being applied to the vessel 102.

When activating gas is not received by the activating switch, i.e. whenever the tool is not being driven, the activating switch 60 directs pressurizing gas to the retraction inlet 78 of the cylinder 80, effecting retraction of the piston rod 85 and release of the pressure upon the vessel 102. Gas contained within the cylinder 80 between the piston 84 and the extension inlet 82 is simultaneously released through the exhaust outlet 90. As the piston rod 85 retracts and the flexible vessel 102 relaxes, the liquid level within the vessel drops, drawing a small portion of liquid back from the conduit 104. An antisyphon feature is thus provided in the sterile liquid source to prevent dripping at the tool.

Employing apparatus in accordance with the present invention, as described herein, a liquid is supplied to a tool concurrently with drive gas, regardless of whether it is a hand-controlled or foot-controlled tool. In addition, sterile liquid is automatically supplied concurrently with drive gas.

While a preferred embodiment has been shown and described, it will be understood that there is no intent to limit the invention by such disclosure, but rather, it is intended to cover all modifications and alternate constructions falling within the spirit and scope of the invention as defined in the appended claims.

I claim:

1. A liquid source system for supplying sterile liquid to a surgical tool comprising a flexible, inelastic vessel containing said sterile liquid, conduit means connecting said vessel to said tool, pressurizing means including a stationary first wall and a stationary second wall generally parallel to said first wall, a plate slidingly mounted between and generally parallel to said first and second walls, to define a vessel receiving zone adapted to receive said flexible, inelastic vessel between said plate and said first wall, and gas activatable cylinder means for urging said plate toward and away from said first wall when said flexible vessel is disposed within the vessel receiving zone, said gas activatable cylinder being connected by activating gas conduit means to sensor means adapted to sense exhaust gas from said tool and provide activating gas to said cylinder whereby liquid is supplied to said tool concurrently with drive gas, said sensor means comprising a low pressure amplifier having an inlet connected to exhaust conduit means from said tool, an amplifying gas inlet connected to an amplifying gas source and an amplifying gas outlet connected to an amplifying gas inlet of a high pressure amplifier having an activating gas inlet connected to an activating gas source and an activating gas outlet connected to said urging means.

2. A system as defined in claim 1 wherein said gas activatable cylinder includes a first member secured to said second wall and an extendible second member secured to said plate.

3. A system as defined in claim 1 wherein said conduit means connecting said vessel to said tool is connected to said vessel in the uppermost region of said vessel when said vessel is located within said vessel-receiving zone.

* * * * *